US00PP11503P

United States Patent [19]

Twomey

[11] Patent Number: Plant 11,503

[45] Date of Patent: Sep. 5, 2000

[54] HYBRID TEA ROSE PLANT NAMED 'TWOPAUL'

[76] Inventor: Jerry F. Twomey, 194 Avocado St., Leucadia, Calif. 92024

[21] Appl. No.: 09/220,902

[22] Filed: Dec. 24, 1998

[51] Int. Cl.[7] ..... A01H 5/00

[52] U.S. Cl. ..... Plt./140

[58] Field of Search ..... Plt./139, 140, 150, Plt./151

[56] References Cited

U.S. PATENT DOCUMENTS

| | | | |
|---|---|---|---|
| P.P. 7,157 | 2/1990 | Christensen | Plt./151 |
| P.P. 7,902 | 7/1992 | Marciel | Plt./140 |
| P.P. 9,404 | 12/1995 | Davidson | Plt./140 |

*Primary Examiner*—Howard J. Locker

[57] ABSTRACT

A new rose cultivar of the Hybrid Tea class characterized by having a red flower with heavy petal substance, non-fading, compact plant, free and continous bloomer. This plant has been designated as 'TWOPAUL'. It is being marketed in the USA under the tradename of 'Dream Red'.

1 Drawing Sheet

The present invention relates to a new and distinctive cultivar of rose plant of the Hybrid Tea class, which was originated by my crossing 'Keepsake' as the seed parent with an unnamed seedling ('Evening Star'×'Trumpeter') as the pollen parent.

Among the novel characteristics possessed by the new cultivar which distinguish it from:

(a) All other cultivars of which I am aware are: (1) Well formed hybrid tea bud and flower with excellent substance. (2) Continuous mass of bloom. (3) Blooms maintain form for long period — 8 to 9 days. (4) Flowers carried above bush of compact growth.

(b)

*Seed parent.*—Pink blend flower, Hybrid Tea.

*Pollen parent.*—seedling — Red flower, Floribunda.

Asexual reproduction of the new rose cultivar by budding, as performed at Wasco, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (RHSCC). The terminology used in the color description herein refers to plate numbers in the aforementioned color chart, e.g. "53A" is plate "53A" of The Royal Horticultural Society Colour Chart.

Parentage:

*Seed parent.*—'Keepsake', not patented.

*Pollen parent.*—unnamed seedling ('Evening Star'× 'Trumpeter').

Class: Hybrid Tea.

The following observations are made of specimens grown outdoors in Monterey, Calif., in the month of August 1998.

FLOWER

Blooming habit:

A. Bud:

(1) *Size.*—Sepals enclosed, 20–22 mm from base of sepals to top of bud.

(2) *Form.*—Ovoid.

(3) *Sepals.*—26 to 28 mm in length; 6 to 8 mm extension beyond bud; no serration shown on sepal edges. Generally 3 out of 5 sepals show appendages on each side, 3 to 5 mm length. Sepals show glandular development on edges. Heavy cotton matting on inner surface, fine matting on outer surface. Outside color — 146B; inside — 195B–195D.

(4) *Peduncle.*—Length — 65 to 70 mm. Surface — small fine prickles, with few glandular hairs. Strength — firm. Color — 146B, shaded — 181B.

(5) *Receptacle.*—Shape — full rounded: 15–17 mm diameter. Color — 146B.

(6) *Color.*—When sepals first divide, outside bud petals near to 44C.

B. Bloom:

(1) *Size.*—When open — 8 to 8.5 cm.

(2) *Borne.*—3–5 per stem.

(3) *Form.*—Globular, uniform, when fully open.

(4) *Petalage.*—Average—26–28.

(5) *Color.*—Early open: outer petals upper surface — 46A lower surface 46C, inner petals: upper surface 46B, lower surface 46C. Aging: Tones of 57A on upper and lower surfaces.

C. Petals:

(1) *Texture.*—Very firm.

(2) *Appearance.*—Flexed; satiny.

(3) *Form.*—Ruffled with heavy substance.

(4) *Arrangement.*—Regular.

(5) *Petaloids in center.*—Average 4 to 6.

(6) *Persistence.*—Long lasting, petals persist.

(7) *Fragrance.*—Slight.

(8) *Lasting quality.*—On plant 9–10 days; cut 6–7 days.

REPRODUCTIVE ORGANS

A. Stamen:

(1) *Arrangement.*—Uniform.

(2) *Number.*—Average 230–250.

(3) *Length.*—Average — 6 to 8 mm.

(4) *Filaments.*—Color — Close to 47B.
(5) *Anthers.*—Color — Close to 23C.
(6) *Pollen.*—Color — Close to 23C.

B. Pistil:
(1) *Styles.*—Length: 5 to 10 mm extending into ovary: 260 to 270; color: near to 61A; no white hairs.
(2) *Stigma.*—Color — Close to 158D.
(3) *Ovary.*—Shape — rounded; 9–10 mm center cross-section at sepal base.

C. Hips: Dose not set seed.

PLANT

A. Form: Bushy.
B. Growth: Vigorous; Height: average — 1.5 m.
C. Stem length: Basal break to flower bud tip: average — 1 m.
D. Foliage: Compound of 3 to 5 leaflets on bloom stem; 5 to 7 leaflets on main canes.
(1) *Mature side.*—5 leaflet — tip of leaflet to stipule base 15–17 cm.
(2 ) *Quantity.*—Stems well covered.
(3) *Color.*—New foliage upper side close to 147B; under side near 147C. Old foliage upper side near to 147A; under side near to 147B.
(4) *Shape.*—Oval with center pointed.
(5) *Texture.*—Firm, leathery, very glossy.
(6) *Edge.*—Serration on outer edge. Average 5 points per 1 cm, with up to 1½ mm peak.
(7) *Rachis.*—Glandular hair on upper side; lower side: 5–7 hooked prickles 2–3 mm length, spaced 1½–2 cm apart.
(8) *Stipules.*—Length 2.5 cm; auricle to 5–6 mm. Edge of stipule to tip of auricle with many glandular hairs.

E. Resistance to disease: Powdery mildew excellent; black-spot good;, rust fair.
F. Wood:
*New wood.*—Color close to 147B, Bark — smooth.
*Old wood.*—Color close to 148A; Bark — smooth.
G. Thorns on mature wood:
*Size.*—8–10 mm.
*Number per* 10 *cm.*—Primary wood 6–7 thorns; Secondary wood same.
*Shape.*—Hooked downward.
*Color.*—Close to 176B.
H. Winter hardiness: Good.

I claim:

1. A new and distinct rose cultivar of the hybrid tea class, substantially as herein shown and described.

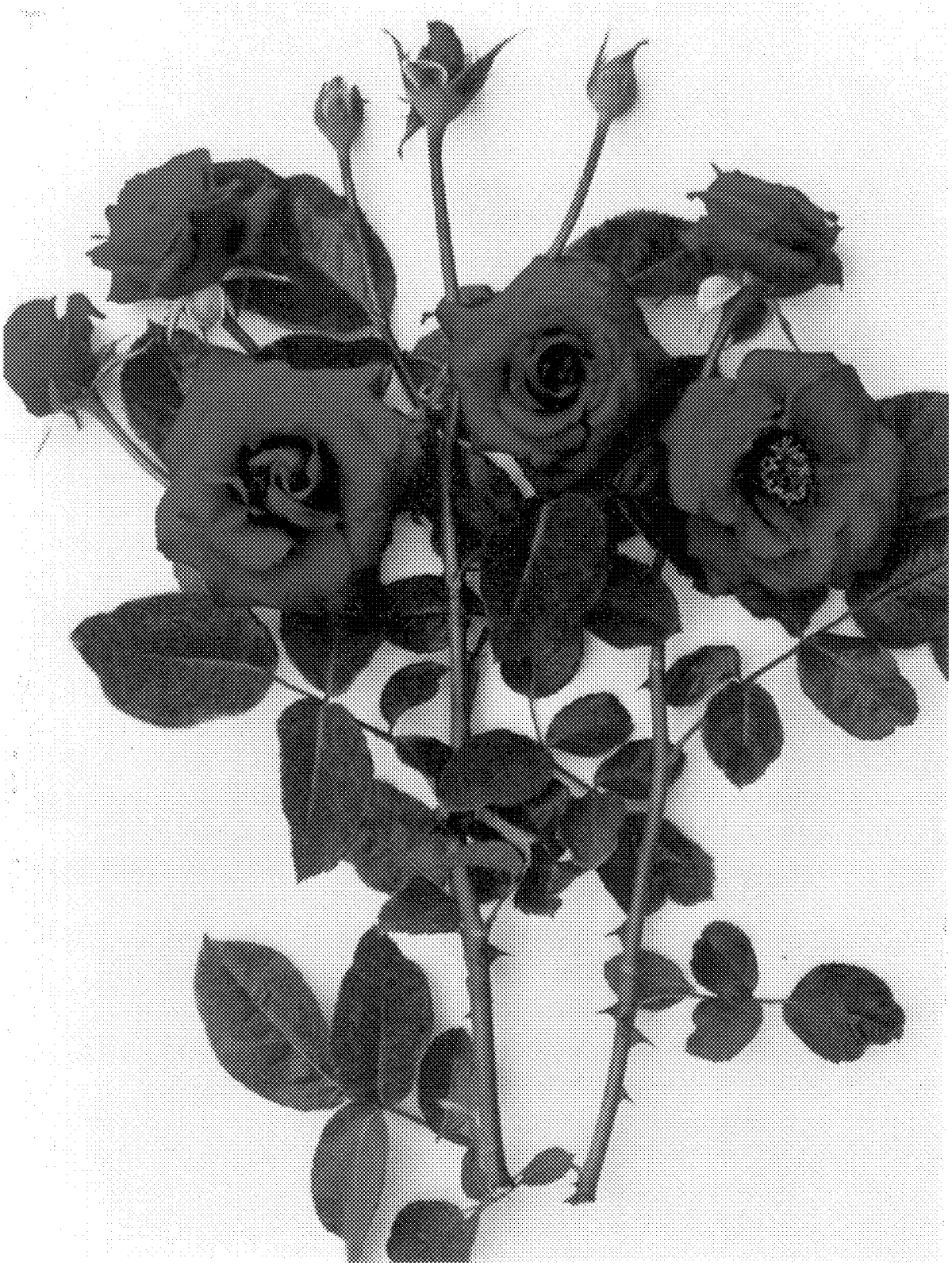

* * * * *